(12) United States Patent
Biffi (10) Patent No.: US 11,534,468 B2
(45) Date of Patent: Dec. 27, 2022

(54) COMPOSITION BASED ON PROBIOTICS AND USES THEREOF

(71) Applicant: LAC2BIOME S.R.L., Milan (IT)

(72) Inventor: Andrea Biffi, Urgnano (IT)

(73) Assignee: LAC2BIOME S.R.L., Milan (IT)

( * ) Notice: Subject to any disclaimer, the term of this patent is extended or adjusted under 35 U.S.C. 154(b) by 17 days.

(21) Appl. No.: 16/770,011

(22) PCT Filed: Dec. 6, 2018

(86) PCT No.: PCT/IB2018/059694
§ 371 (c)(1),
(2) Date: Jun. 4, 2020

(87) PCT Pub. No.: WO2019/111189
PCT Pub. Date: Jun. 13, 2019

(65) Prior Publication Data
US 2021/0236566 A1    Aug. 5, 2021

(30) Foreign Application Priority Data

Dec. 6, 2017   (IT) .......................... 102017000141330

(51) Int. Cl.
| | |
|---|---|
| *A61K 35/747* | (2015.01) |
| *A61P 17/02* | (2006.01) |
| *A61K 8/99* | (2017.01) |
| *A61K 35/745* | (2015.01) |
| *A61K 35/00* | (2006.01) |
| *A61Q 17/00* | (2006.01) |
| *A61Q 17/04* | (2006.01) |
| *A61Q 19/08* | (2006.01) |

(52) U.S. Cl.
CPC .............. *A61K 35/747* (2013.01); *A61K 8/99* (2013.01); *A61K 35/745* (2013.01); *A61P 17/02* (2018.01); *A61K 2035/115* (2013.01); *A61Q 17/005* (2013.01); *A61Q 17/04* (2013.01); *A61Q 19/08* (2013.01)

(58) Field of Classification Search
CPC .......................... A61K 2035/115; A61Q 17/04
See application file for complete search history.

(56) References Cited

U.S. PATENT DOCUMENTS

| | | | |
|---|---|---|---|
| 2005/0158291 | A1 | 7/2005 | Breton |
| 2010/0226892 | A1 | 9/2010 | Gueniche |
| 2013/0095086 | A1 | 4/2013 | Lu et al. |
| 2016/0296569 | A1* | 10/2016 | Guglielmetti ........ A61K 35/747 |

FOREIGN PATENT DOCUMENTS

| | | | | |
|---|---|---|---|---|
| EP | 1322318 A1 | | 7/2003 | |
| WO | WO 02/28402 A1 | | 4/2002 | |
| WO | WO2017060468 A1 | * | 4/2017 | ........... A61K 35/745 |

OTHER PUBLICATIONS

Silvia Balzaretti et al, The vaginal isolate Lactobacillus paracasei LPC-S01 (DSM26760) is suitable for oral administration, Frontiers in Microbiology, Sep. 2015, vol. 6, Article 952 (Year: 2015).*
Alejandra Vasquez et al., Oral administration of Lactobacillus and Bifidobacterium strains of intestinal and vaginal origin to healthy human females: Re-isolation from faeces and vagina, Microbial Ecology in Health and Disease. 2005; 17: 15-20 (Year: 2005).*
Joseph McLaughin et al., Propionibacterium acnes and Acne Vulgaris: New Insights from the Integration of Population Genetic, Multi-Omic, Biochemical and Host-Microbe Studies, Microorganisms 2019, 7, 128 (Year: 2019).*
Audrey Gueniche et al., Probiotics for photoprotection, Dermato-Endocrinology 1:5, 275-279; Sep./Oct. 2009 (Year: 2009).*
Agatha Schwarz etal, The Short-Chain Fatty Acid Sodium Butyrate Functions as a Regulator of the Skin Immune System, Journal of Investigative Dermatology (2017) 137, 855e864, publication date: Nov. 23, 2016 (Year: 2016).*
Balzaretti et al., "The vaginal isolate Lactobacillus paracasei LPC-S01 (DSM 26760) is suitable for oral administration", Frontiers in Microbiology, 2015, vol. 6, Article 952.
Chapat et al., "Lactobacillus casei reduces CD8+ T cell-mediated skin inflammation", Eur. J. Immunol., 2004, 34: 2520-2528.
Wang et al., "Children with atopic dermatitis show clinical improvement after Lactobacillus exposure", Clinical & Experimental Allergy, 2015, 45: 779-787.

* cited by examiner

*Primary Examiner* — Mark V Stevens
*Assistant Examiner* — Alparslan Asan
(74) *Attorney, Agent, or Firm* — James S. Keddie; Bozicevic, Field & Francis LLP (57) ABSTRACT

The present invention relates to a composition comprising probiotics, preferably based on bacteria, in particular of the genus *Lactobacillus*, to be used for the purpose of preventing and/or treating the disorders affecting the skin, in particular inflammatory disorders, in particular autoinflammatory disorders of dermatological interest such as atopic dermatitis. Furthermore, the composition of the invention is useful for preventing and/or reducing the damage induced by UV radiation, in particular skin aging.

5 Claims, 2 Drawing Sheets

Fig.1

Fig.2

COMPOSITION BASED ON PROBIOTICS AND USES THEREOF

CROSS-REFERENCE TO RELATED APPLICATIONS

This application is a § 371 national phase of International Application No. PCT/IB2018/059694, filed on Dec. 6, 2018, which claims the benefit of Italian Application No. 102017000141330, filed on Dec. 6, 2017, which applications are incorporated by reference herein.

FIELD OF THE INVENTION

The present invention relates to a composition comprising probiotics, preferably based on bacteria, in particular of the genus *Lactobacillus*, to be used for the purpose of preventing and/or treating disorders affecting the skin, in particular inflammatory disorders, in particular autoinflammatory disorders of dermatological interest such as atopic dermatitis. Furthermore, the composition of the invention is useful for preventing and/or reducing the damage induced by UV radiation, in particular skin aging.

PRIOR ART

Human skin is colonised by a rich microbiome. In the past it used to be thought that this aspect represented a potential source of infection, whereas today there is an awareness of the fact that the human microbiota, in general, and therefore also the skin microbiota, performs important and useful functions in the host, not only because of its ability to oppose the adhesion and development of skin pathogens, but also because of its ability to dialogue and interact with the immune system.

When a dysbiosis occurs at the skin level, probiotics can act as modulators and restore balance to the skin microbiota.

In the past decade, the use of new technologies has facilitated taxonomic analysis of the skin microbiota, whose bacterial population can amount to about 1010 species of microorganisms belonging to over 25 phyla, the most representative of which are Actinobacteria, Firmicutes, and Proteobacteria.

Various skin diseases have been linked to alterations in the skin microbiome.

For example, in the case of acne, *P. acnes* is considered the bacterium mainly associated therewith; in these conditions, in fact, the increased production of sebum provides an optimal environment for its growth.

The conventional approach to these problems is to use antibacterials, i.e. to use topical disinfectants and antibiotics.

On the one hand, antibiotics are undoubtedly effective, but, besides also eliminating beneficial bacteria, they carry the risk of sensitization and potential adverse events, particularly in the case of prolonged use of broad-spectrum antibiotics.

For this reason, the Applicant has identified, as a new solution for restoring balance to the skin microbiota, the use of probiotic compositions, based, in particular, on the use of bacteria belonging to the genus *Lactobacillus*. In fact, the Applicant has found that a composition comprising probiotics belonging to the genus *Lactobacillus* are capable of preventing, or in any case mitigating, the action of bacteria that are dangerous for the skin, such as *P. acnes*, precisely, and are thus able to:

1) contribute to preventing and/or treating disorders affecting the skin;
2) promote the normal healing process; and
3) promote and/or improve normal re-epithelialization and/or cicatrization processes.

BRIEF DESCRIPTION OF THE FIGURES

The present invention is described in detail below and illustrated by way of example also with the aid of the appended figures, in which:

FIG. 1 graphically shows the adhesion of *P. acnes* in terms of percentage of live, viable cells adhering following:

1a: pre-stimulation by contact of keratinocytes with the tested probiotics;

1b: co-incubation of keratinocytes with *P. acnes* and with the tested probiotics;

1c: incubation of keratinocytes with the tested probiotics, after the eukaryotic cells have been challenged with the pathogen.

Where 100 represents the adhesion of *P. acnes* in the absence of stimulation by the probiotics, the inhibition capacity of the tested strains has been expressed as the % reduction of adhesion by *P. acnes* compared to the positive control. In particular, FIG. 1a shows the ability of both probiotic strains to prevent the adhesion of *P. acnes*, in a similar % (42% for *L. casei* DG® and 35% for *L. paracasei* LPC-S01).

FIG. 1b shows the ability of the strain *L. casei* DG® to reduce adhesion by 17%, whereas the strain *L. paracasei* LPC-S01 stood at 9%. Mixing the strains produced a statistically significant reduction in the adhesion of *P. acnes*, which stood at 42%, a distinctly higher percentage than observed both for the strains considered individually and the sum of their effects.

FIG. 1c shows a statistically significant synergistic effect tied to the mixture of the 2 probiotics, which showed to be capable of reducing the adhesion of *P. acnes* by 42%. The individual probiotics, by contrast, showed an ability to reduce adhesion which was less than half that of the mixture, 18% for *L. casei* DG and 11% for *L. paracasei* LPC-S01.

DETAILED DESCRIPTION OF THE INVENTION

One aspect of the present invention relates to a composition comprising probiotics, preferably one or more probiotic bacteria, for use in the treatment and/or prevention of disorders and/or pathologies, preferably of an inflammatory type, affecting the skin, preferably of a dermatological type.

Said disorders and/or pathologies affecting the skin are selected from: dermati tis, preferably associated with irritations and/or excoriations, acne, infections, skin inflammations, erythema, ulcers, psoriasis, atopic dermatitis, otitis, rhagades, fistulas, haemorrhoids, and any other skin disorder or lesion with or without the presence of an ongoing inflammatory process and/or combinations and/or complications and/or outcomes thereof.

Said disorders and/or pathologies affecting the skin are preferably associated with or caused by pathogens. That is, the composition is particularly effective not only for preventive/prophylactic purposes, but also for treatment/therapeutic purposes, i.e. after a challenge with said pathogens.

According to a preferred aspect of the present invention, the composition can also favour/facilitate/promote/speed up the wound healing process and/or re-epithelialization and/or cicatrization processes.

Said pathogens are preferably selected from: bacteria, fungi, yeasts, viruses and combinations thereof.

Said pathogens are preferably selected from among bacteria, and said bacterial pathogens are preferably selected from: genus *Propionibacterium*, preferably the species *acnes*; *Staphylococcus*, preferably *epidermidis*, *aureus*, warned, *pyogenes, mitis Corynebacterium* ssp; *Pseudomonas*, preferably *aeruginosa*; *Acinetobacter*, preferably *johnsonii*; *Streptococcus*, preferably *pyogenes*; *Micrococcus* ssp., and *Brevibacterium* ssp.

Furthermore, the composition comprising probiotics, preferably one or more probiotic bacteria, as described in detail below, is indicated for shielding the skin and/or the lips and/or the conjunctivae, against UV radiation, UV-A and/or UV-B. In other words, the composition is indicated for preventing and/or attenuating the damage and/or effects due/related to exposure to UV radiation, UV-A and/or UV-B. The composition is preferably indicated for preventing and/or attenuating skin aging.

From this viewpoint, the composition comprising probiotics, preferably one or more probiotic bacteria, as described in detail below, has cosmetic purposes.

The uses of the composition are preferably related/due to the immunomodulating action of the probiotics contained in the composition, preferably the probiotics as defined and described below. Said immunomodulation involves a modulation, preferably a reduction of the expression of at least one cytokine selected from: hematopoietic cytokines, preferably hematopoiesis growth factors and/or CSF; primary inflammatory cytokines, preferably IL-1 and/or TNF; anti-inflammatory and/or immunosuppressive cytokines, preferably IL-10 and/or TGF-β; secondary inflammatory cytokines (chemokines); cytokines regulating a specific immune response, preferably IL-2, and combinations thereof. Said immunomodulation preferably involves a modulation, preferably a reduction of the expression of at least one cytokine, selected from: IL-1ß, IL-10, IL-8, TSLP and combinations thereof.

In this regard we shall note that cytokines are non-antigen-specific polypeptide mediators acting as communication signals between the cells of the immune system and between the latter and various organs and tissues. They are produced by different types of cells and once freed in the body they induce specific reactions in adjacent cells (paracrine effect), in others very far away (endocrine effect) or in those that created them (autocrine effect). In particular, those produced by the cells of the immune system, such as interleukins and chemokines, play a fundamental role in regulating and activating our mechanisms of defence and in inflammatory processes. The complex network of cytokines maintains a balance between pro-inflammatory and anti-inflammatory effects. An imbalance between pro-inflammatory and anti-inflammatory cytokines, as well as an uncontrolled production of cytokines, can result in diseases of an inflammatory type, allergies or autoimmune pathologies.

TSLP (thymic stromal lymphopoietin) is a protein belonging to the cytokine family and it plays an important role in the maturation of T-cell populations through the activation of cells exhibiting the antigen. TSLP is mainly produced by non-hematopoietic cells such as fibroblasts, epithelial cells and various types of stromal cells, and its expression is tied to many pathological states, including asthma, inflammatory arthritis, atopic dermatitis, eczema, eosinophilic esophagitis and other allergic conditions.

In particular, the Applicant has shown that when keratinocytes are exposed to probiotics, the latter are capable of exerting an immunomodulating effect, as is evident from the evaluation of cytokine assays on the cellular supernatant. In particular, the expression of IL1B, IL10 and IL8 was observed to be reduced by the probiotic strains considered individually, in particular by *L. paracasei* LPC-S01. The effect of containing cytokine expression appeared more evident following a challenge of the keratinocytes with LPS.

As regards TSLP, the contact with the probiotics determined a reduction in this indicator compared to the baseline expression (of keratinocytes not stimulated by the probiotic). Pre-stimulation of keratinocytes with LPS did not result in an increase in the levels of TLSP, a phenomenon to be expected, as it is known that other molecules are more stimulating for the Toll-like receptors of LPS. The probiotic strains, considered individually and in a mixture, showed to be effective in conditioning the expression of this indicator. The indicator is of considerable interest, as it is overexpressed in some skin pathologies such as atopic dermatitis. Furthermore, this cytokine is considered a key mediator at the functional interface between keratinocytes and dendritic cells.

According to a preferred aspect of the invention, the composition is useful in the processes of wound healing and/or re-epithelialization and/or cicatrization of injured skin and/or skin affected by disorders.

Therefore, the data clearly indicate that probiotics, in particular the tested strains, are capable of exerting an anti-inflammatory and/or immunomodulating effect on keratinocytes and therefore on the skin.

In general, considering the effects described here, the composition based on probiotics described here is useful for the purpose of restoring balance to the skin microbiota.

In the context of the present invention, "skin" means the first line of defence against the external environment; in particular, this defence is performed through the action of the keratinocytes disseminated in the outermost skin layer (epidermis), where they can induce the secretion of cytokines and chemokines in order to deliver a message of alert to the deeper layers of the skin, thus generating an inflammatory response. In the course of their development, keratinocytes migrate from the deeper layers to the more superficial layers, with a progressive deposition of keratin, which is responsible for the protective action with respect to the underlying cells.

In the context of the present invention, "skin aging" means a wholly natural and inevitable physiological process that occurs in all individuals. As time passes, the skin undergoes structural changes caused by a series of factors of different origin, which bring about a loss of skin moisture, the appearance of fine wrinkles, loss of elasticity, hyperkeratosis and the formation of hyperpigmented patches called "age spots".

Said aging is preferably an intrinsic—or chronological—aging that substantially depends on genetic (or intrinsic) factors. Alternatively, said skin aging is extrinsic—or due to environmental factors—i.e. caused by external factors (extrinsic factors).

Generally speaking, intrinsic aging usually begins after 25 years of age. It usually involves a series of changes that generally lead to a thinning and/or yielding of the skin structure.

Extrinsic aging is preferably caused by the aggression of external agents and/or environmental factors preferably selected from: UV radiation (responsible for photoaging), cigarette smoking, alcohol abuse, pollution, continuous contact with irritant substances and combinations thereof.

The damage and/or the effects due/related to exposure to UV radiation are preferably selected from: erythema, pigmentation, keratosis, hyperkeratosis, skin reddening, sunburn, burns, actinic photoaging or solar elastosis, cortical cataract, pterygium, reactivation of oral herpes, skin damage of any nature, preferably damage to the lips and/or conjunctivae, skin melanoma, squamous cell carcinoma of the skin, basal cell carcinoma, squamous cell carcinoma of the cornea or conjunctivae and/or combinations and/or complications and/or outcomes thereof.

In the context of the present invention "restoring balance to the skin microbiota" means restoring the qualitative-quantitative physiological composition of the skin microbiota, understood as the entire set of microorganisms present on the skin, and thus restoring the physiological cutaneous microbial ecology.

In the context of the present invention, "challenge" means any experimental test or challenge or trial involving contamination with microorganisms of different species and a subsequent evaluation of the changes in the microbial load, usually by means of a plate count of the number of the live microorganisms at regular intervals of time.

In the context of the present invention, "probiotic", in accordance with the definition given by the FAO and WHO, means: "Live microorganisms which when administered in adequate amounts confer a health benefit on the host". In other words, probiotics are microorganisms that demonstrate to be capable, once taken in suitable amounts, of exerting functions which are beneficial for the body.

Said microorganisms are preferably selected from: bacteria, fungi, yeasts and combinations thereof.

According to a preferred aspect of the invention, the bacteria belong to at least one genus selected from: *Lactobacillus, Bifidobacterium, Bacillus, Propionibacterium, Streptococcus, Lactococcus, Aerococcus* and *Enterococcus*. More preferably the bacteria belong to the genus *Lactobacillus*.

According to a further preferred aspect of the invention, the bacteria of the genus *Lactobacillus* belong to at least one species selected from: *Lactobacillus paracasei, Lactobacillus acidophilus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus collinoides, Lactobacillus paraplantarum, Lactobacillus pentosus, Lactobacillus plantarum, Lactobacillus pontis, Lactobacillus reuteri, Lactobacillus rhamnosus, Lactobacillus sakei, Lactobacillus salivarius, Lactobacillus sanfranciscensis* and combinations thereof.

More preferably, the lactobacilli are of the species *Lactobacillus paracasei*, preferably the strain *Lactobacillus paracasei* DG® CNCM I-1572 and/or the strain *Lactobacillus paracasei* LPC-S01.

Both strains were isolated and deposited by SOFAR S.p.A., in particular, the bacterial strain *Lactobacillus paracasei* DG was deposited with the National Collection of Cultures of Microorganisms (CNCM) of the Pasteur Institute in Paris on May 5, 1995, with the deposit number CNCM I-1572. The strain was initially called *Lactobacillus casei* DG sub. *casei*.

The bacterial strain *Lactobacillus paracasei* LPC-S01 was deposited with the DSMZ, with the accession number DSM26760.

Said strains are particularly effective for the uses described here when they are used in association and/or combination, in fact, they show an additive and/or even synergistic effect.

According to a further preferred aspect of the invention, the bacteria of the genus *Bifidobacterium* belong to at least one species selected from: *B. animalis, B. bifidum, B. breve, B. infantis, B. longum, B. adolescentis, B. catenulatum, B. angulaturn, B. asteroides, B. bourn, B. choerinum, B. coryneforme, B. cuniculi, B. denticolens, B. dentium, B. gallicum, B. gallinarum, B. indicum, B. inopinaturn, B. lactis, B. magnum, B. merycicum, B. minimum, B. pseudocatenulatum, B. pseudolongum, B. pullorum, B. ruminantium, B. saeculare, B. subtile, B. thermacidophilum, B. thermophilum* and *B. tsurumiense*; more preferably selected from: *Bacillus clausii, Bacillus subtilis, Bacillus coagulans, Bacillus megaterium Bacillus halodurans, Bacillus thuringiensis, Bacillus insolitus* and *Bacillus marinus*.

According to a further preferred aspect of the invention, the bacteria of the genus *Propionibacterium* belong to at least one species selected from: *P. shermanii, P. acnes, P. australiense, P. avidum, P. cyclohexanicum, P. freudenreichii, P. granulosum, P. jensenii, P. microaerophilum, P. propionicum* and *P. thoenii*.

According to a further preferred aspect of the invention, the bacteria of the genus *Streptococcus* belong to at least one species selected from: *Streptococcus thermophilus, Streptococcus salivarius, Streptococcus agalactiae, Streptococcus anginosus, Streptococcus bovis, Streptococcus canis, Streptococcus constellatus, Streptococcus downei, Streptococcus dysgalactiae, Streptococcus equinus, Streptococcus ferus, Streptococcus infantarius, Streptococcus iniae, Streptococcus intermedius, Streptococcus milleri, Streptococcus mitis, Streptococcus mutans, Streptococcus oralis, Streptococcus orisratti, Streptococcus parasanguinis, Streptococcus peroris, Streptococcus pneumoniae, Streptococcus pseudopneumoniae, Streptococcus pyogenes, Streptococcus ratti, Streptococcus tigurinus, Streptococcus sanguinis, Streptococcus sobrinus, Streptococcus suis, Streptococcus uberis, Streptococcus vestibularis, Streptococcus viridans* and *Streptococcus zooepidemicus*.

According to a further preferred aspect of the invention, the bacteria of the genus *Lactococcus* belong to at least one species selected from: *L. chungangensis, L. formosensis, L. fujiensis, L. garvieae, L. lactis, L. piscium, L. plantarum, L. raffinolactis* and *L. taiwanensis*.

According to a further preferred aspect of the invention, the bacteria of the genus *Aerococcus* belong to at least one species selected from: *A. urinae, A. sanguinicola, A. christensenii, A. suis, A. urinaeequi* and *A. urinaehominis*.

According to a further preferred aspect of the invention, the bacteria of the genus *Enterococcus* belong to at least one species selected from: *Enterococcus avium, Enterococcus durans, Enterococcus faecalis, Enterococcus faecium, Enterococcus gallinarum, Enterococcus haemoperoxidus, Enterococcus hirae, Enterococcus malodoratus, Enterococcus moraviensis, Enterococcus mundtii, Enterococcus pseudoavium, Enterococcus raffinosus* and *Enterococcus solitarius*.

According to a further preferred aspect of the invention, the yeasts belong to the genus *Saccharomyces*, more preferably the species *Saccharomyces cerevisiae* and/or *Saccharomyces boulardii*.

The microorganisms, preferably the bacterial strain *L. casei* DG® and/or the bacterial strain *Lactobacillus paracasei* LPC-S01, are preferably used live, i.e. they are used as probiotics.

Alternatively, the microorganisms, preferably the bacterial strain *L. casei* DG® and/or the bacterial strain *Lactobacillus paracasei* LPC-S01 are dead or tyndallized.

In a further embodiment, the microorganisms, preferably the bacterial strain *L. casei* DG® and/or the bacterial strain *Lactobacillus paracasei* LPC-S01, are used in the form of a lysate and/or extract, i.e. they are used as a paraprobiotic.

Alternatively, the microorganisms, preferably the bacterial strain *L. casei* DG® and/or the bacterial strain *Lactobacillus paracasei* LPC-S01, are used in the form of bacterial products, supernatants, derivatives, preferably bacterial derivatives, preferably metabolites, metabolic bioproducts, post-biotics, cell wall and components thereof, exopolysaccharides, or compounds containing immunogenic components, preferably selected from: ribosomes and glycoproteins, immunostimulant derivatives, such as glucans and other polysaccharides, lipopolysaccharides and any component of the supernatant.

In general, said microorganisms are individual microorganisms or combinations of microorganisms, or consortia, of any microbial species indicated in the QPS list of the EFSA.

In any case, the composition of the invention can comprise any type of microorganism, in particular bacteria, having a probiotic effect/action/function and/or microorganisms as defined above, preferably bacteria, which are capable of stably colonising the skin, the gut and/or other regions of the body, taking away space from pathogenic microorganisms/bacteria and/or directly combating them. The cosmetic composition and/or composition for medical use as described above preferably comprises a combination of the strains specified above with other microorganisms as described above, preferably selected from: bacteria, fungi, yeasts and combinations thereof.

The microorganisms, preferably the bacteria, are present in a minimum amount that is sufficient to enable a temporary colonization of the skin, gut and/or other regions of the body. Said amount preferably varies between $10^6$ and $10^{11}$ units of microorganisms, more preferably $10^8$ and $10^9$ units of microorganisms, said amount preferably being an amount/dose per day (daily).

The composition further comprises excipients and/or further pharmaceutically accepted substances and/or carriers.

The composition of the present invention preferably further comprises a substance selected from: plasma, PRP, cicatrizing substances, re-epithelializing substances, wetting agents, hydrating agents, emollient agents, adsorbent, analgesic and phlebotonic agents, anti-inflammatories, muscle relaxants, peptidic and/or proteic substances and/or proteins, such as collagen, substances belonging to connective tissue, such as glycosaminoglycans, preferably chondroitin sulphate, and/or combinations thereof.

In one embodiment of the present invention, the composition is formulated for applications preferably of a topical type, preferably in the form of a cream, gel, oil, emulsions, sprays, gauzes, patches, bandages, lotions, mousses, ointments, pastes, or liquid formulations in which the composition is preferably added extemporaneously prior to application on the skin.

In one embodiment of the present invention, the composition is used for the transplant of skin microbiota. In the context of the present invention, transplant of skin microbiota means the administration, preferably topical, of the skin microbiota, and/or part thereof, of healthy subjects, who have no skin disorders, in order to re-establish a correct balance, thereby treating any dysbiosis that may be present. For these purposes, the composition of the invention preferably comprises bacteria, preferably the bacterial strain *L. casei* DG® and/or the bacterial strain *Lactobacillus paracasei* LPC-S01, and optionally also fungi, viruses, peptides, proteic and/or peptidic substances, carbohydrates, vitamins, trace elements or any other substance characterising the microbiota of the skin and/or other regions of the body. For such purposes, said composition is preferably used in combination with: amino acids, supplements, vitamins, trace elements such as zinc and selenium, macro and micro nutrients, enzymes and/or prebiotic substances such as fructooligosaccharides (FOS), galactooligosaccharides (GOS), inulin, guar gum and/or combinations thereof.

In one embodiment of the present invention, the composition is formulated for oral administration, preferably as a solid formulation, preferably as pills, capsules, tablets, granular powder, hard-shelled capsules, orally dissolving granules, sachets or lozenges.

Alternatively, the composition is formulated as a liquid, preferably for extemporaneous preparations.

Alternatively, the composition is in a form capable of exerting a topical action, for example as an enema, cream, spray, gel, patch, lotions, mousses, ointments, pastes, or liquid formulations in which the composition is preferably added and/or prepared extemporaneously prior to application on the skin.

According to a preferred embodiment of the invention, the composition of the invention is used in combination with: amino acids, supplements, vitamins, trace elements such as zinc and selenium, macro and micro nutrients, enzymes and/or prebiotic substances such as fructooligosaccharides (FOS), galactooligosaccharides (GOS), inulin, guar gum or combinations thereof.

Example

Bacterial Strains and Cells

By way of example, the invention was demonstrated using the following bacterial strains:

*L. casei* DG® (*Lactobacillus paracasei* CNCM I-1572)

*L. paracasei* LPC-S01;

*L. casei* DG®+*L. paracasei* LPC-S01 1:1 mixture.

The bacterial strains were cultured in a selective medium consisting of MRS (de Man Rogosa Sharpe) for 16 hours at 37° C. Once growth reached the stationary phase, a sample of bacteria was collected, to be used for the tests. They were washed several times with PBS (Phosphate Buffered Saline) and centrifuged in order to remove the spent culture medium. Use was made of live cells in the stationary phase because in this phase rather than in the stationary one the bacteria induce a smaller immune response.

All of the tests described below were carried out in triplicate.

Normal human keratinocytes maintained in culture with suitable supplements were used for the experiments.

*Propionibacterium acnes* (*P. acnes*) CCUG 50865 (purchased from the CCUG (Culture Collection, University of Goteborg)) was cultured for 16 hours at 37° C. in Cooked Meat Medium (both liquid and solid), prepared according to the supplier's instructions. The bacterial concentration was subsequently determined by spectrophotometry, with readings at O.D. 600 nm, and was used for the adhesion tests.

Adhesion Test and Challenge of the Cell Line with the Pathogen

The keratinocytes were seeded at 37° C. with 5% $CO_2$ in wells of cell culture plates and allowed to grow until reaching confluence (i.e. about $10^5$ total cells). The seeding ratio was $2.5 \times 10^5$ cells/0.32 cm2 (i.e. a cell density of $7.8 \times 10^5$ cells/cm2). At the time of the experiment, the medium was removed, the cells were washed with an antibiotic-free medium, and bacteria were then added for the tests, which were carried out according to the different protocols described below.

1) Adhesion of Strains to Keratinocytes.

After the number of keratinocytes per well had been determined, the strains of *L. paracasei* were added at MOI 1:10 (10^5 cells and 10^6 CFU of bacteria per well). The strains were tested in a 1:1 ratio, both individually and in combination.

The bacteria were left in contact with the cells maintained at 37° C. with slight shaking for 60 minutes. At the end of the incubation the medium was removed and the cells were washed with a sterile medium to remove the bacteria that had not adhered to the cell monolayer.

In order to calculate the number of adherent bacteria, the cells were detached and lysed and the bacteria were counted by supravital staining after seeding in agarized MRS medium.

2) Adhesion Exclusion Test.

After the number of keratinocytes was determined for each well, the strains of *L. paracasei* were added to the cells in a 1:1 ratio, both individually and in combination.

The bacteria were left in contact with the cells maintained at 37° C. with slight shaking for 60 minutes. At the end of the incubation the medium was removed and the cells were washed with a sterile medium to remove the bacteria that had not adhered to the cell monolayer.

*P. acnes* (at a 1:10 MOI) was then placed in contact with the cells allowed to incubate for 60 minutes at 37° C. At the end of the incubation the culture medium was removed and the non-adhering bacteria were eliminated by washing with sterile medium.

In order to calculate the number of *P. acnes* adhering to the keratinocytes, the cells were detached and lysed and the bacteria were counted by supravital staining after seeding in 5% sheep's blood agar under anaerobiosis for 48-72 hours at 37° C. Wells with keratinocytes that had not been pre-incubated with the strains of *L. paracasei*, but rather inoculated with *P. acnes* alone, were used as a positive control for the adhesion of *P. acnes* (*P. acnes* adhesion control), while wells with cells that had not been incubated with any bacteria were used as a negative control (sterility control).

3) Test of Adhesion Competition

After the number of keratinocytes per well had been determined, the strains of *L. paracasei* were added (both individually and in a 1:1 ratio) simultaneously with *P. acnes*. The bacteria were added at an overall MOI of 1:10 and in a 1:1 probiotic:pathogen ratio.

The bacteria were left in contact with the cells at 37° C. with slight shaking for 60 minutes. At the end of the incubation the medium was removed and the cells were washed with a sterile medium to remove the bacteria that had not adhered to the cell monolayer.

In order to calculate the number of *P. acnes* adhering to the keratinocytes, the cells were detached and lysed and the bacteria were counted by supravital staining after seeding in 5% sheep's blood agar under anaerobiosis for 48-72 hours at 37° C. Wells with keratinocytes inoculated with *P. acnes* alone were used as a positive control (*P. acnes* adhesion control), while wells with cells that had not been incubated with any bacteria were used as a negative control (sterility control).

4) Test of Adhering Pathogen Removal.

After the number of keratinocytes per well had been determined, *P. acnes* was added (MOI 1:10).

The bacteria were left in contact with the cells maintained at 37° C. with slight shaking for 60 minutes. At the end of the incubation the medium was removed and the bacteria that had not adhered to the cell monolayer were removed by repeated washings with sterile medium.

Then the strains of *L. paracasei* (both individually and in combination in a 1:1 ratio) were left in contact with the cells maintained at 37° C. with slight shaking for 60 minutes. At the end of the incubation the medium was removed and the cells were washed with a sterile medium to remove the bacteria that had not adhered to the cell monolayer.

In order to calculate the number of *P. acnes* adhering to the keratinocytes, the cells were detached and lysed and the bacteria were counted by supravital staining after seeding in 5% sheep's blood agar under anaerobiosis for 48-72 hours at 37° C.

The keratinocytes treated with *P. acnes* were used as a positive control (*P. acnes* adhesion control), while keratinocytes that had not been treated with bacteria were used as a negative control (sterility control).

The tests performed both on the individual strains in pure form and on the 1:1 mixture were repeated twice.

1) Adhesion of Strains to Keratinocytes—Results

The results of this test showed the ability of the strains, taken individually and also in combination, to adhere to the keratinocytes. In particular, the strain *L. casei* DG® showed a greater capacity of adhesion to keratinocytes than *L. paracasei* LPC-S01. The adhesion capacity observed for the combination is thus presumably attributable to the contribution provided by the strain *L. casei* DG®.

TABLE 1

| | Adhesion (No of bacteria-CFU/well) |
|---|---|
| *L. casei* DG | $139 \times 10^2$-$141 \times 10^2$ |
| *L. paracasei* S01 | $18.2 \times 10^2$-$21.8 \times 10^2$ |
| 1:1 mixture | $98 \times 10^2$-$122 \times 10^2$ |
| *Propionibacterium acnes* | $700 \times 10^2$-$2000 \times 10^2$ |

Adhesion Exclusion Test (Pre-Treatment of Eukaryotic Cells with Probiotics and Subsequent Incubation with the Pathogen)—Results As noted above, the monolayer of keratinocytes was initially exposed to contact with the probiotics and subsequently, following removal of the non-adhering bacteria, to contact with *P. acnes*, which was then removed by washing; this was followed by a quantification of the residual viability of *P. acnes*.

Figure 1:
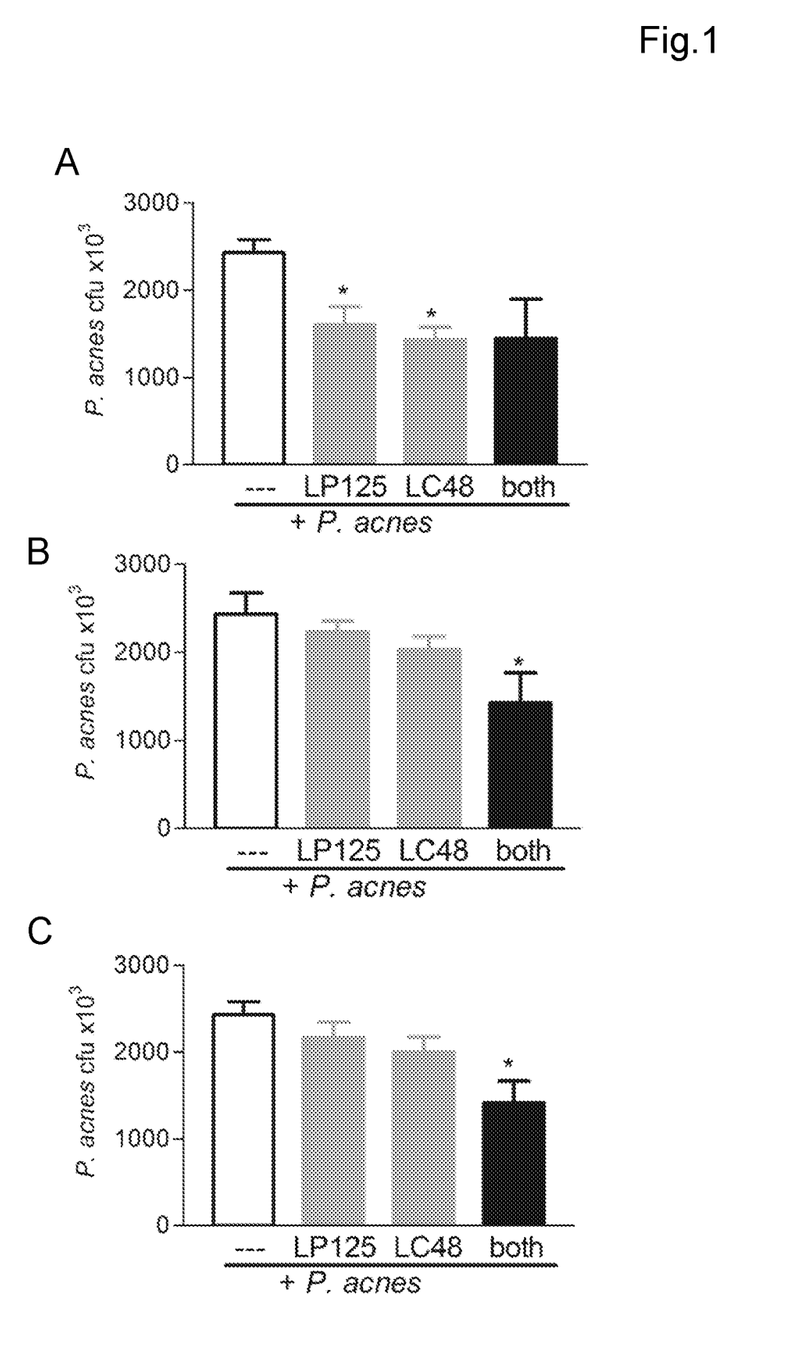

The negative control is represented by eukaryotic cells without stimulation by contact with bacteria, whereas the positive control is represented by the ability of *P. acnes* to adhere to keratinocytes without any pre-treatment with probiotics. FIG. 1A shows the results regarding the adhesion of *P. acnes*, in terms of the percentage of live, viable cells adhering following pre-stimulation of the keratinocytes by contact with the different probiotics tested. Where 100 represents the adhesion of *P. acnes* in the absence of stimulation with probiotics, the inhibition capacity of the tested strains was expressed as a % reduction of adhesion by *P. acnes* compared to the positive control.

Both probiotic strains showed an ability to prevent the adhesion of *P. acnes*, in a similar % (42% for *L. casei* DG® and 35% for *L. paracasei* LPC-S01).

Adhesion competition test (co-incubation of eukaryotic cells with the probiotics and with the pathogen)—Results During these tests, the reduction, if any, of the adhesion of *P. acnes* to keratinocytes was assessed following a simultaneous treatment of the cell line with the probiotics and the pathogen, with the aim of evaluating the possible competitive inhibition effect exerted by the probiotics when co-incubated with *P. acnes*.

Keratinocytes treated with *P. acnes* were used as a positive control, while keratinocytes that had not been treated with bacteria were used as a negative control (sterility control).

FIG. 1B graphically shows the results related to the adhesion of *P. acnes* in terms of the percentage of live, viable cells adhering following co-incubation of the keratinocytes with *P. acnes* and with the different tested probiotics. As previously described, where 100 represents the adhesion of *P. acnes* in the absence of stimulation by the probiotics, the inhibition capacity of the tested strains was expressed as a % of reduction of adhesion by *P. acnes* compared to the positive control.

In this mode of interaction between probiotics and pathogen, the strain *L. casei* DG® showed an ability to reduce adhesion by 17%, whereas the strain *L. paracasei* LPC-S01 stood at 9%. The combination of the strains produced a statistically significant reduction in the adhesion of *P. acnes*, which stood at 42%, a distinctly higher percentage than the one observed for the strains considered individually, and also higher than the sum of their effects.

Test on the removal of adhering pathogens (pre-treatment of the eukaryotic cells with the pathogen and subsequent incubation with the probiotic)—Results During these tests, any reduction in the adhesion of *P. acnes* to the keratinocytes was assessed following a pre-treatment of the cell line with the pathogen and subsequent incubation with the probiotics following the removal of the non-adhering pathogen.

Keratinocytes treated with *P. acnes* were used as a positive control, while keratinocytes that had not been treated with bacteria were used as a negative control (sterility control).

FIG. 1C graphically shows the results related to the adhesion of *P. acnes* in terms of the percentage of live, viable cells adhering following incubation of the keratinocytes with the different tested probiotics, after the challenge of eukaryotic cells with the pathogen. As previously described, where 100 represents the adhesion of *P. acnes* in the absence of probiotics, the inhibition capacity of the tested strains was expressed as a % reduction of adhesion by *P. acnes* compared to the positive control.

In these tests too, as in the case of the co-incubation protocol, an interesting, statistically significant synergistic effect was observed, tied to the combination of the 2 probiotics, which showed to be capable of reducing the adhesion of *P. acnes* by 42%. The individual probiotics, by contrast, showed an ability to reduce adhesion that was less than half that of the mixture, 18% for *L. casei* DG® and 11% for *L. paracasei* LPC-S01.

Immunomodulation Tests

The immunomodulation tests were carried out with the aim of verifying whether the probiotic strains have the ability to modulate the release of cytokines by human keratinocytes exposed to the negative stimulation of bacterial lipopolysaccharides (LPS).

Normal human keratinocytes were seeded as described above in cell culture plates and upon reaching confluence they were used for the experiments. In particular, the cell monolayers were washed and incubated in a fresh medium containing no antibiotics. Then the strains of *L. paracasei* were added individually and in combination in a 1:1 ratio at an MOI of 1:10.

The bacteria were left in contact with the keratinocytes for 120 minutes at 37° C. with slight shaking. In some cases the cells were pre-stimulated (challenged for about 24 h) with LPS at a final concentration of 100 ng/ml.

At the end of the incubation the medium was removed, the cells were washed with a sterile medium in order to eliminate the bacteria that had not adhered to the cells and subsequently kept in a culture medium for 24 hours at 37° C.

At the end of the incubation, the culture medium was collected in order to quantify the cytokines produced by means of the ELISA assay (IL-10, IL-1 beta, IL-8, thymic stromal lymphopoietin [TSLP]), whereas the levels of cyclooxygenase-2 (COX-2) and activated NF-kB (induced by LPS or IL-1beta) were determined by Western Blot on the total proteins extracted from the lysed keratinocytes.

These markers were selected because they are involved both in acute phlogosis and allergic dermatitis, as well as in the chronic associated phlogosis.

In particular, IL-10 is considered anti-inflammatory, and its production generally increases in parallel to that of powerful pro-inflammatory cytokines like IL-1 beta. TSLP is a cytokine that modulates the action of lymphocytes and is involved in the development of chronic keratitis.

Results

The ability of the tested strains to stimulate the immune response of keratinocytes was evaluated according to the above described protocol. The tests were focused on determining cytokines (IL-8, IL-1beta, and IL-10) and evaluating the activation of 2 markers, COX-2 and NF-kB.

COX-2 (cyclooxygenase-2) represents an inducible marker produced by a limited number of cell types in response to a specific inflammatory stimulus. It is overexpressed in several neoplasms, including skin neoplasms. NF-kB (nuclear factor kappa-light-chain-enhancer of activated B cells) is a protein complex with the function of a transcription factor, produced by all cell types in response to various stimuli, including those of an inflammatory nature.

The cultured keratinocytes were exposed to the probiotics *L. paracasei*, *L. casei* DG® and *L. paracasei* LPC-S01, and the combination of the two strains in a 1:1 ratio according to the procedures already described. The cellular supernatants were then assayed to determine the cytokines, with particular reference to those of an anti-inflammatory type which could be assayed in the keratinocytes placed in contact with probiotic strains. The assay results are summarized in FIG. 2 and graphically show the assay of IL-10, IL-1 beta and IL-8 in the cell supernatants, expressed in pg per ml of supernatant, obtained by means of the ELISA test.

Figure 2:
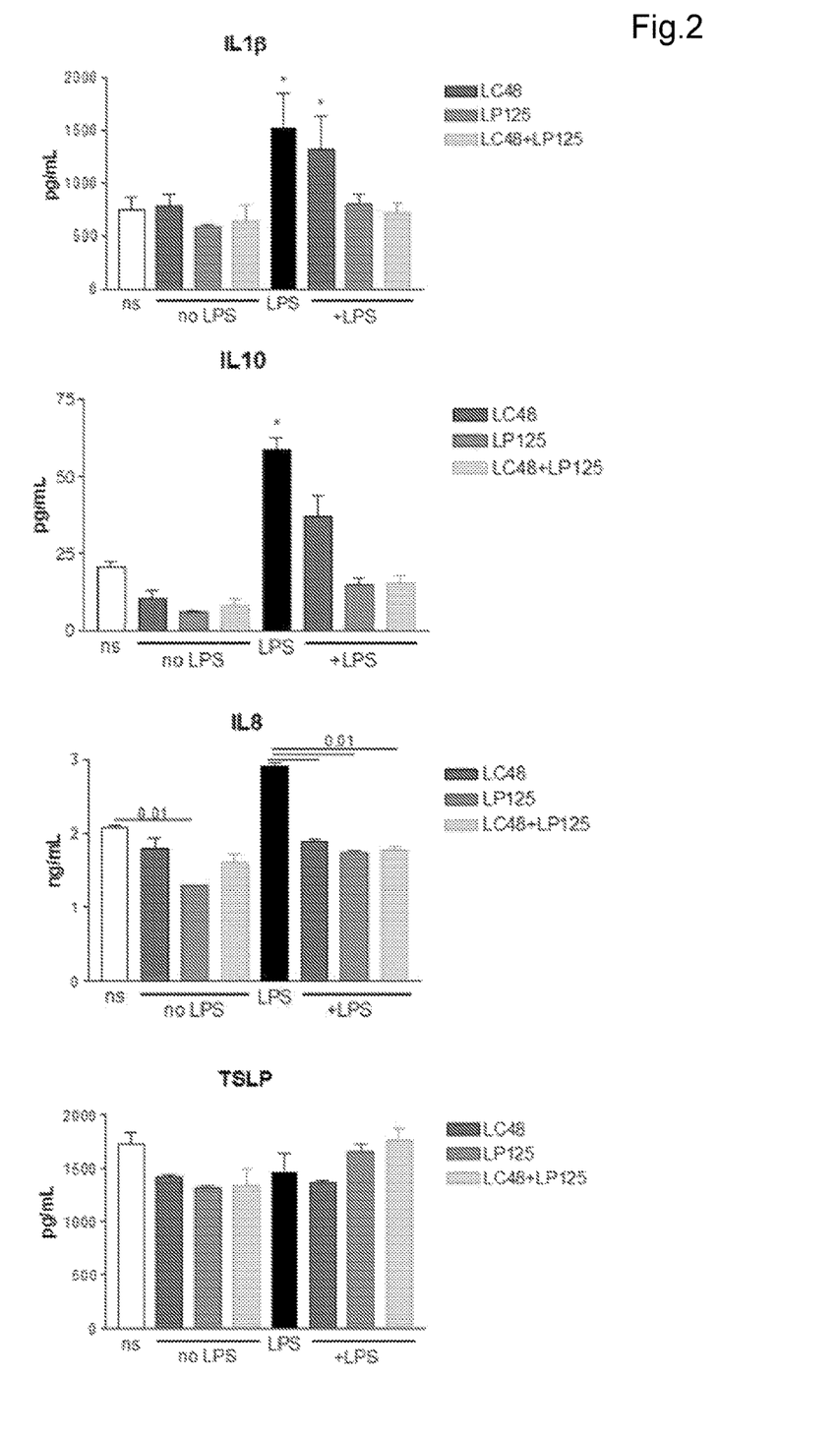
FIG. 2 graphically shows the results of the assay on the cytokines IL-10, IL-1beta, IL-8 and TSLP in the supernatants of the cells, expressed in picograms (pg) per ml of supernatant, obtained by means of the ELISA test.

The detailed evaluations of the results obtained made it possible to conclude as follows:

IL1ß: levels of expression of a few nanograms per ml of supernatant of the keratinocytes. The contact with the probiotics did not bring about a statistically significant reduction in this cytokine compared to the baseline expression (of keratinocytes not stimulated by the probiotic). *L. paracasei* LPC-S01 showed a moderately positive impact compared to *L. casei* DG® and one that was comparable to that of the combination. Analogous considerations also apply in the case of pre-stimulation of the keratinocytes with LPS in order to maximise the immune response.

IL-10: levels of expression of several tens of pg per ml of keratinocytes' supernatant. The contact with the probiotics brought about a reduction in this cytokine compared to the baseline expression (of keratinocytes not stimulated by the probiotic). *L. paracasei* LPC-S01 showed a moderately positive impact compared to *L. casei* DG® and comparable to that of the combination. Analogous considerations also apply in the case of pre-stimulation of the keratinocytes with LPS in order to maximise the immune response.

IL-8: levels of expression of a few nanograms per ml of keratinocytes' supernatant. The contact with the probiotics brought about a reduction in this cytokine compared to the baseline expression (of keratinocytes not stimulated by the probiotic). *L. paracasei* LPC-S01 showed a positive impact compared to *L. casei* DG® and comparable to that of the combination. In the case of pre-stimulation of the keratinocytes with LPS in order to maximise the immune response, both probiotics showed an ability to positively influence the control of the cytokine, with an analogous potential both for the probiotics considered individually and the mixture.

TSLP: levels of expression of a few nanograms per ml of keratinocytes' supernatant. The contact with the probiotics brought about a reduction in the indicator compared to the baseline expression (of keratinocytes not stimulated by the probiotic). The probiotic strains, considered individually and in combination, showed to be effective in conditioning the expression of this indicator. The indicator is of considerable interest, since it is overexpressed in some skin pathologies such as atopic dermatitis. Furthermore, this cytokine is considered a key mediator at the functional interface between keratinocytes and dendritic cells.

The evaluation of the levels of expression of COX-2 made it possible to show that the levels of this marker do not seem to undergo particular changes following contact of the keratinocytes with the probiotics compared to the baseline levels, except for a moderate action of containment due to contact with *L. paracasei* LPC-S01. The treatment with LPS showed an increase in the levels of expression of COX-2 by the eukaryotic cells, an increase that was effectively contained and limited by the action of the probiotics. The presence of *L. paracasei* LPC-S01 eliminates the expression of the marker to a larger degree compared to *L. casei* DG®, whereas the combination of the 2 probiotic strains did not seem to show any action.

As the expression of IL8 and COX-2 is regulated by means of the transcription factor NF-kB, a qualitative assessment was made of the release of NF-kB by keratinocytes exposed to the probiotics. The results demonstrate that, in the absence of the inflammatory stimulus represented by LPS, the expression of the marker does not seem to be detectable. However, it is activated by the bacterial lipopolysaccharides via the phosphorylation of p65. The 2 probiotic strains manifested an ability to contain the expression of NF-kB, with particular reference to *L. paracasei* LPC-S01, the presence of which, both as a single strain and in a mixture with DG, showed to be particularly effective in containing the expression of LPS-induced NF-kB.

Evaluation of the Reduction of Damage Caused by UV

The ability of the probiotic strain LPC-S01 to reduce the damage caused by UV radiation was evaluated on a complete 3D in vitro reconstructed skin model which reproduces the compartments of the dermis and epidermis, thus making it possible to study the modifications of the extracellular matrix of the dermis and the differentiation of the viable skin layers (Full Thickness Skin Model). The study regarded the evaluation of the effect of the strain LPC-S01 on the activation of the inflammasome in response to UV irradiation. The strain LPC-S01 was applied directly on the surface of the 3D skin model, incubated overnight and then rinsed with saline solution to remove the excess product.

The tissue was lightly scratched and then exposed to 1 MED (minimal erythematogenic dose) of UV in order to mimic normal sun exposure. The activation of the inflammation was tested 4 and 24 hours after exposure to the UV radiation. Tissue treated with a saline solution and exposed to UV radiation was used as a positive control. A saline solution was used as a negative control.

Histomorphological Analysis with Haematoxylin/Eosin Staining

At the end of the treatment, the tissues were washed with saline solution and fixed in 10% formalin. For each sample, the biological replicates (n=3) were included in the same paraffin blocks and 2 non-consecutive 5 μm sections were cut and collected. The tissue sections were stained with haematoxylin and eosin. The histological samples were analysed with an optical microscope (20× and 40× magnification) and the morphological changes in the tissue and the cytotoxic effect were evaluated.

Immunostaining of NFkB

Marking NFkB enables its translocation from the cell cytoplasm into the nucleus to be evaluated; its translocation is in fact capable of activating the inflammatory process. NFkB was marked using the immunostaining technique known in the art. In particular, use was made of a primary Anti-NFkB (Abcam) antibody and a secondary antibody stained with the fluorophore Alexa 555 and a counterstaining with DAPI to highlight the cell nuclei. The images were acquired with a fluorescence microscope with 40× magnification.

Quantification of Interleukin 1β by ELISA

The antibodies were adsorbed on an ELISA plate and the samples were then incubated. A secondary antibody was added to form a "sandwich". The quantification was based on a standard curve. The data were acquired by means of spectrophotometric measurements.

Results of the Reduction of Damage Caused by UV 4 hours after exposure to UV radiation, the untreated tissue (positive control) showed a morphology that was not altered, but with cells damaged by UV radiation in the lower part of the epidermis. After 4 h the tissue treated with the strain LPC-S01 showed no substantial change in the morphology or general architecture of the tissue or in the burn damage present in the lower epidermis. 24 hours after exposure to UV radiation, the tissue showed typical alterations of the epidermis due to burns, with pyknotic nuclei, epidermis and dermis with alterations. The administration of the strain LPC-S01 showed no improvements in preventing the morphological changes in the tissue induced by the UV radiation.

Table 2 summarizes the results of the quantification of NFkB translocation 4 hours after exposure to UV radiation.

TABLE 2

|  | Negative control | Positive control | LPC-S01 |
|---|---|---|---|
| Number of Translocations | 25.7 | 47.2 | 22.4 |

4 hours after irradiation, the positive control showed a high number of NFkB translocations, particularly in the suprabasal layer of the epidermis.

The treatment with the probiotic LPC-S01 was able to inhibit the nuclear translocation of NFkB to a significant degree compared to the positive control.

Furthermore, the strain LPC-S01 also showed to be capable of reducing the cytoplasmic levels of NFkB.

Finally, the secretion of IL-1β showed an increase 4, 8 and 24 hours after the insult with UV radiation. The administration of the probiotic LPC-S01 enabled the secretion of IL-1β to be reverted 4, 8 and 24 hours after the insult. In particular, a significant reduction was noted 8 and 24 hours after the insult.

TABLE 3

| | secretion of IL-1β | | | | | | | | |
|---|---|---|---|---|---|---|---|---|---|
|  | NC 4 h | PC 4 h | S01 4 h | NC 8 h | PC 8 h | S01 8 h | NC 24 h | PC 24 h | S01 24 h |
| IL-1 β (pg/ml) | 2.12 | 2.74 | 2.10 | 2.49 | 3.18 | 1.92 | 3.13 | 4.78 | 3.44 |

The probiotic LPC-S01 thus showed an ability to prevent the activation of inflammation by inhibiting the traslocation of NFkB into the nucleus of cells subjected to insult by UV radiation. Furthermore, the strain S01 showed a direct effect in reducing the levels of inflammation by reducing the levels of the pro-inflammatory interleukin 1β 4, 8 and 24 hours after the irradiation insult.

The invention claimed is:

1. A method of attenuating dermatological damage and/or effects due/related to an action of the bacteria *P. acnes* comprising:
   topically administering a composition comprising a combination of bacteria of the strain *Lactobacillus paracasei* CNCM 1-1572 and bacteria of the strain *Lactobacillus paracasei* DSM26760 to a subject having a dermatological condition caused by *P. acnes*.

2. A method for treatment of disorders and/or pathologies of an inflammatory type affecting skin in the reduction and/or treatment of the symptoms and/or effects associated with said disorders/pathologies and/or to promote a wound healing process and/or re-epithelialization and/or cicatrization processes, comprising topically administering a combination of probiotics to the skin, wherein the probiotics comprise bacteria of the strain *Lactobacillus paracasei* CNCM 1-1572 and bacteria of the strain *Lactobacillus paracasei* DSM26760.

3. The method according to claim 2, wherein said disorders and/or pathologies affecting the skin are selected from: dermatitis, acne, infections, skin inflammations, erythema, ulcers, psoriasis, atopic dermatitis, otitis, rhagades, fistulas, hemorrhoids, any other skin disorder or lesion with the presence of an ongoing inflammatory process and/or combinations and/or complications and/or outcomes thereof.

4. The method according to claim 1, wherein the composition further comprises microorganisms selected from: bacteria, fungi, yeasts or combinations thereof and wherein the bacteria belongs to at least one genus selected from: *Lactobacillus, Bifidobacterium, Bacillus, Propionibacterium, Streptococcus,* or *Lactococcus*.

5. The method according to claim 3, wherein the composition is for topical use and wherein the composition is in the form of a cream, gel, oil, emulsions, sprays, gauzes, patches, bandages, lotions, mousses, ointments, pastes, or liquid formulations for extemporaneous preparations.

* * * * *